Feb. 10, 1959 R. S. MOORE Plant Pat. 1,808
MINIATURE ROSE PLANT
Filed May 19, 1958
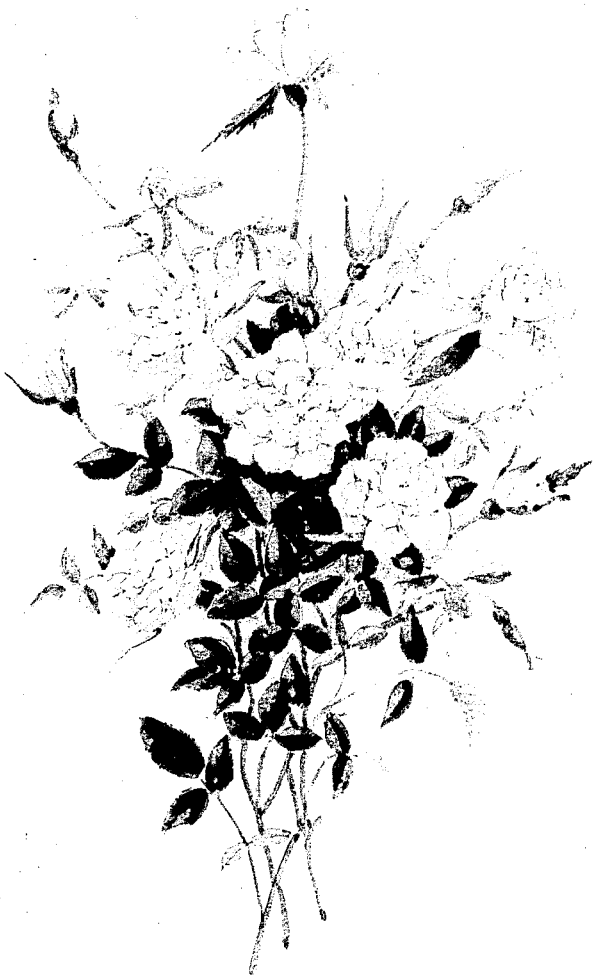
WITNESS
Addison E. Avery
INVENTOR
Ralph S. Moore
Webster & Webster
ATTYS.

United States Patent Office

Plant Pat. 1,808
Patented Feb. 10, 1959

1,808

MINIATURE ROSE PLANT

Ralph S. Moore, Visalia, Calif.

Application May 19, 1958, Serial No. 736,418

1 Claim. (Cl. 47—61)

This invention relates to a new and distinct miniature rose plant of bush type, bearing attractive flowers which open well in all weather, and which flowers—in general effect—are light red or deep pink, with a glowing undertone when freshly opened.

The variety was originated by me in my nursery located at Visalia, California, and under conditions of careful control and observation, as a cross between two unnamed seedlings; the seed parent having been Rosa Wichuriana×Floradora, while the pollen parent was Oakington Ruby×Floradora. All of such prior varieties are unpatented.

After origination of the instant variety of miniature rose plant I successfully reproduced it, in my nursery located as aforesaid, both by cuttings and budding; such reproductions having been observed to run true in all respects to the original plant of the variety.

The present variety of miniature rose plant is distinctively characterized—in comparison to the Oakington Ruby, and which in general it most nearly resembles—by faster growth; and flowers which are produced more freely, more double, of a brighter red color, and in maturity dimensioned nearly as deep as broad.

Additional characteristics of the present variety of miniature rose plant are propagation more easily and rapidly than most other varieties of the class; strikes roots quickly from either hard or soft cuttings; and develops into sizable, salable, florists' potted plants faster than any other miniature rose variety.

Further, neat compact habit of growth, together with the color, quantity, and quality of the bloom, makes the variety especially desirable for use as a potted plant, as well as a low hedge or garden border plant.

A moderate but distinct apple scent or fragrance of the flowers is another distinguishing characteristic of the variety.

The figure of the drawing illustrates a spray, including foliage, buds, and flowers.

Referring now specifically to the new and distinct variety of miniature rose plant, the following is a detailed description thereof in outline; all major color plate identifications being by reference to British Colour Council Horticultural Color Chart, except where otherwise indicated, or where common terms of color definition are employed.

Type: Hardy; dwarf; bush; greenhouse; outdoors; seedling; cut flowers; garden decoration; potted plant.
Class: Miniature.

*Flowers*

Continuity: Continuous.
Fragrance: Moderate apple scent.
Flowers borne: Singly, but sometimes several to stem; on strong, medium length stems.
Quantity of bloom: Abundant, both outdoors and in greenhouse.

Bud:
*Peduncle.*—Medium to long; medium strength; erect; smooth. Color—green.
*Before calyx breaks.*—Size—small. Form—pointed, with foliaceous appendages on the surface of the bud, and with foliaceous parts extending beyond tip of the bud equal to ½ to ¾ or more of its length. Color—green.
*As calyx breaks.*—Color—red.
*As first petal opens.*—Size—small. Form—pointed. Color: outside—Spirea Red (o25), shading to white at base; inside—Spirea Red (o25), shading to Chrysanthemum Crimson (824/1) in the darker portion, and shading to white at base. Opening—opens well in all weather.

Bloom:
*Size when fully open.*—Small, averaging 1" to 1¼".
*Petalage.*—Very double, with from 40 to 60 petals, arranged regularly.
*Form.*—Flat at first, becoming globular; petals remaining at first loosely rolled outward, becoming later at maturity substantially fully rolled outwardly. The flower at maturity becomes nearly as deep as it is broad.

Petals: Thick; leathery, with both inside and outside satiny.
*Shape.*—Outside—obovate, with acute tip. Intermediate—lanceolate. Inside—lanceolate.
*Color.*—Newly opened flower from plant grown in a greenhouse: Outside petal—outside surface—Spirea Red (o25/1), shading to white or near white at base; inside surface—Spirea Red (o25), shading to white or near white at base. Intermediate petal—outside surface—Spirea Red (o25/1), shading to white or near white at base; inside surface—Spirea Red (o25), shading to white or near white at base. Inner petal—outside surface—Spirea Red (o25/2), shading to white or near white at base; inside surface—Spirea Red (o25/1), shading to white or near white at base. A flower that was open for three days on a plant grown in a greenhouse: Outside petal—outside surface—Magenta (27 to 27/1 or 27/2); inside surface—Magenta (27/3). Inside petal—outside surface—Magenta (27/2); inside surface—Magenta (27/1). General color effect—newly opened flower—bright light red; three days open—bright deep pink. Colors become deeper in cool weather.
*Behavior.*—Drop off cleanly.
*Flower longevity.*—Bush in garden—5 to 8 days. Flowers—kept at room temperatures—cut from plant grown outdoors—5 to 7 days. Flowers—kept at room temperatures—cut from plant grown in greenhouse—5 to 6 days.

Reproductive organs:
*Stamens.*—Very few to none.
*Filaments.*—Medium; very few. Color—white, with slight greenish tint.
*Anthers.*—Small. Color—light yellow.
*Pollen.*—Very sparse. Color—lemon.
*Pistils.*—Few.
*Styles.*—Even; short; medium; bunched.
*Stigma.*—White.
*Ovaries.*—All enclosed in calyx.
*Hips.*—Globular. Color—reddish orange. Smooth; walls thin.
*Sepals.*—Long; spear shaped. Color—green.
*Seeds.*—Very few; small.

*Plant*

Foliage:

*Leaves.*—Compound of 3 to 5 leaflets. Abundant; small; glossy, being more glossy outdoors than in greenhouse.

*Leaflets.*—Shape—ovate. Leaflets smaller outdoors than in greenhouse.

*Margin.*—Serrate.

*Color.*—Mature leaves; upper surface—normal green (24–L–7) (Maerz and Paul Dictionary of Color); under surface—lighter normal green (22–G–6) (Maerz and Paul Dictionary of Color). Young leaves—normal green, but upper surface has a very slight bronze tint, while the under surface has a reddish tint.

*Rachis.*—Medium. Upper side—smooth, grooved. Under side—sparsely thorny.

*Stipules.*—Medium length; narrow, with medium points turning out at an angle of about 45 degrees.

Growth:

*Habit.*—Dwarf; bushy; much branched.

*Growth.*—Vigorous.

*Canes.*—Medium.

*Main stems.*—Color—green. Thorns—few; medium length; straight, with short rounded base. Prickles—none. Hairs none.

*Branches.*—Color—green. Thorns—none to few. Prickles—none. Hairs—none.

*New shoots.*—Color—green, tinted bronze red. Thorns—very few. Prickles—none. Hairs—none.

The miniature rose plant and its flowers as herein described may vary in slight detail due to climatic and soil conditions under which the variety may be grown.

The following is claimed:

A new and distinct variety of miniature rose plant of bush type, substantially as described and illustrated, characterized by a hardy, dwarf, bushy, much branched, vigorous growing plant which propagates easily and rapidly, strikes roots quickly from either hard or soft wood, and grows rapidly to maturity; further characterized by very double, red, abundantly borne, very double flowers which open well in all weather, become in full bloom nearly as deep as broad, and have a moderate apple scent; and additionally characterized—in comparison to the Oakington Ruby, by faster growth, and by flowers which are produced more freely, more double, and of a brighter red color.

No references cited.